United States Patent [19]
Zeelen et al.

[11] 4,222,940
[45] Sep. 16, 1980

[54] CYCLIZATION SUBSTRATES, CYCLIZATION PROCESS AND RELATED 11β-AXIALLY-SUBSTITUTED STEROIDS

[75] Inventors: Filippus J. Zeelen, Heesch; Arnoldus I. A. Broess, Rijen, both of Netherlands

[73] Assignee: Akzona Incorporated, Asheville, N.C.

[21] Appl. No.: 953,790

[22] Filed: Oct. 23, 1978

[30] Foreign Application Priority Data

Oct. 25, 1977 [NL] Netherlands ............... 7711667

[51] Int. Cl.³ .............. C07J 5/00; C07C 5/09
[52] U.S. Cl. .............. 260/239.55 R; 260/397.45; 260/397.5; 568/630; 568/633
[58] Field of Search .............. 260/397.5, 239.55 R, 260/397.45

[56] References Cited

FOREIGN PATENT DOCUMENTS

1448873  9/1976 United Kingdom .............. 260/239.55

OTHER PUBLICATIONS

Journal of the American Chem. Soc., Feb. 18, 1976. pp. 1038–1041.
Chim. Ther. 8 No. 4 (1973) pp. 451–454 Article by Boulanger et al.
Experientia 26/7 (1970) pp. 762–763, Article by Baran et al.

*Primary Examiner*—Elbert L. Roberts
*Attorney, Agent, or Firm*—Robert H. Falk; Francis W. Young; Charles A. Wendel

[57] ABSTRACT

There are disclosed substrates of the formula:

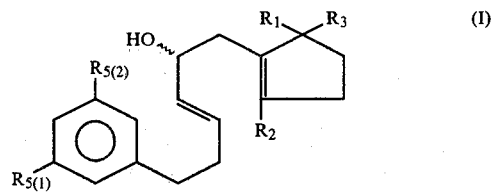

wherein:
(a) $R_1$ is H or $C_1$–$C_4$ alkyl;
(b) $R_2$ is H or $C_1$–$C_4$ alkyl with the proviso that $R_1$ is H when $R_2$ is alkyl, and with the proviso that $R_2$ is H when $R_1$ is alkyl;
(c) $R_3$ is a leaving group including hydroxy, $C_1$–$C_4$ alkoxy, $C_2$–$C_4$ alkoxalkoxy, $C_1$–$C_7$ acyloxy, and trialkylsilyloxy of less than fifteen carbons; and
(d) $R_{5(1)}$ and $R_{5(2)}$ are each H, $C_1$–$C_8$ alkyl, or an optionally esterified or etherified hydroxy group including hydroxy, $C_1$–$C_4$ alkoxy, $C_2$–$C_4$ alkoxyalkoxy, $C_1$–$C_{15}$ trialkylsilyloxy, $C_4$–$C_8$ cycloalkoxy, $C_1$–$C_7$ carboxyacyloxy, or unsubstituted heterocyclic ether of five to seven members, with the proviso that at least one of $R_{5(1)}$ and $R_{5(2)}$ is hydrogen.

A method is disclosed for the cyclization of the compounds of formula I leading to compounds of the following formulae:

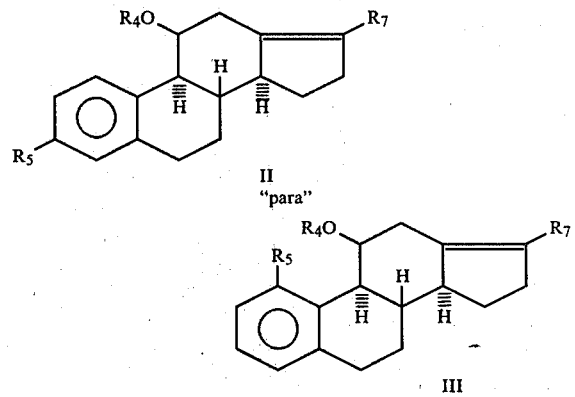

having $R_4$ as defined above, with $R_5$ being $R_{5(1)}$ or $R_{5(2)}$ as defined above, and $R_7$ being $C_1$–$C_4$ alkyl.

28 Claims, No Drawings

CYCLIZATION SUBSTRATES, CYCLIZATION PROCESS AND RELATED 11β-AXIALLY-SUBSTITUTED STEROIDS

The invention relates to the preparation of novel cyclisation substrates for steroidal compounds, and also relates to the conversion of these cyclisation substrates into novel steroidal compounds, in particular, 11β-substituted-oxy-steroids of the oestrane series.

The known 11β-oxy-steroids include compounds of pharmacological interest, for example, 11β-methoxy-oestradiol, 11β-methoxy-oestrone and the corresponding 11β-ethoxy compounds, as well as the 3-ethers thereof, and are known as potent oestrogenic compounds (see Dutch Pat. 134 220).

As is also known, the introduction by chemical means of an oxygen substituent into the 11-position of a steroid is associated with substantial difficulties, both in the total synthesis and in the normal preparation. Generally, recourse is made by one skilled in the art to microbiological oxidation methods.

One such oxidation method is, for example, the method described in the Dutch Patents 121 957 and 122 324, wherein 3-oxo-$\Delta^{5(10),9(11)}$-steroids of the oestrane series are oxidized with molecular oxygen under alkaline conditions to 11β-hydroperoxy compounds, which may be converted by reduction into 11β-hydroxy compounds. These latter compounds may, for example, be converted into some of the pharmacologically interesting 11β-alkoxy-A-aromatic compounds noted above (see for example U.S. Pat. No. 3,472,884 and U.S. Pat. No. 3,519,654, and Dutch Patent Specification No. 134 220). The 3-oxo-$\Delta^{5(10),9(11)}$ starting material may, for example be prepared by total synthesis (see for example the U.S. Pat. No. 3,052,672).

The present invention relates to novel cyclisation substrates of the formula:

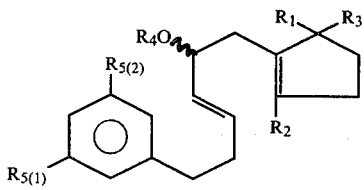

wherein:

(a) $R_1$ is H or alkyl of one to four carbon atoms;
(b) $R_2$ is H or alkyl of one to four carbon atoms, with the proviso that $R_1$ is H when $R_2$ is alkyl, and with the proviso that $R_2$ is H when $R_1$ is alkyl;
(c) $R_3$ is a suitable leaving group selected from the group consisting of hydroxy, alkoxy of one to four carbons, alkoxy of two to four carbons, acyloxy of one to about seven carbon atoms, and trialkylsilyloxy of less than fifteen carbons;
(d) $R_4$ is H, hydrocarbyl of one to fourteen carbons, carboxyacyl of two to twelve carbons, trialkylsilyl of less than fifteen carbons, and heterocyclic of five to seven members and four to six carbons; and
(e) $R_{5(1)}$ and $R_{5(2)}$ are each H, alkyl of one to eight carbons, or an optionally esterified or etherified hydroxy group selected from the group consisting of hydroxy, alkoxy of one to four carbons, alkoxy-alkoxy of two to four carbons, carboxyacyloxy of one to seven carbons, trialkylsilyloxy of one to fifteen carbons, cycloalkoxy of four to eight carbons, or unsubstituted heterocyclic ether of five to seven members and from four to six carbons, with the proviso that at least one of $R_{5(1)}$ and $R_{5(2)}$ is hydrogen.

Surprisingly, it has now been found that the cyclisation of a cyclisation substrate of formula (I):

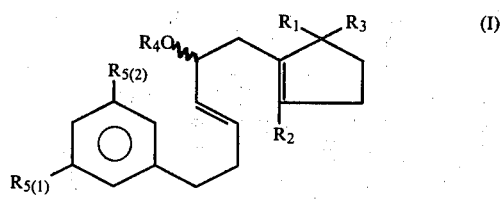

leads stereo-selectively to axially-substituted steroid compounds of formula II and III having $R_4$ and $R_5$ ($R_{5(1)}$ or $R_{5(2)}$) as described above:

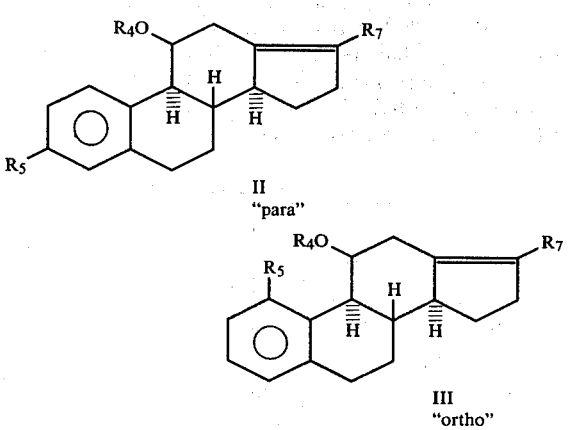

which may be represented in shorthand notation by the following formula (positions indicated in small arabic numerals):

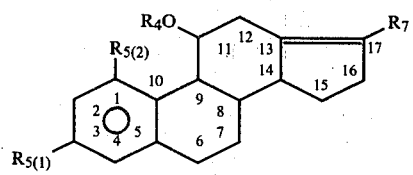

which is more recognizable to those skilled in the art. $R_7$ is an alkyl moiety of one to four carbon atoms.

In formula I, II and III, most preferably $R_1$ and $R_2$ are H or $CH_3$, $R_3$ is OH, $R_4$ is methyl, benzyl or pivaloyl, one of $R_{5(1)}$ and $R_{5(2)}$ is H and the other is $OCH_3$ or trialkylsilyloxy of three to twelve carbon atoms, and $R_7$ is $CH_3$.

When $R_{5(1)}$ is the same as $R_{5(2)}$, the resultant compounds are of course identical, but when $R_{5(1)}$ is not $R_{5(2)}$, two isomers result from the cyclisation: the proportions of which are strongly influenced by the cyclisation conditions and the choice of the substituents $R_4$, $R_{5(1)}$ and $R_{5(2)}$.

The cyclisation substrates of formula (I) are novel compounds which may be prepared in several ways each of which are known to those skilled in the art. The invention is therefore characterized by the preparation of novel compounds with the general formula (I) by steps which are in themselves known to those in the art.

The invention is also characterized by the cyclisation of novel cyclisation substrates of formula (I) to the novel and biologically active steroid compounds of formulae II and III that are axially substituted in the 11-position.

Referring to the Flow Diagram below, the cyclisation substrate (I) may, for example, be prepared by condensing in Reaction (or step) (a) an acetylide of formula (IV) with an aldehyde of formula (V) to give a propargyl alcohol of formula (VI). In step (b) the trans-allyl alcohol of formula (VIIa) is obtained by reduction of the triple bond, and this may optionally be etherified or esterified to (VIIb), after which (VII) is hydrolyzed to the dioxo compound (VIII) which is condensed in step (d) to the cyclopentenone of formula (IX). When $R_2$ is alkyl of one to four carbons, the ketone obtained is reduced to an alcohol [formula I, $R_1$ is H, $R_2$ is alkyl of one to four carbons and $R_3$ is OH], or when $R_2$ is H, it is reacted with a compound $R_1Li$, for example methyl-lithium, ethyl-lithium, butyl-lithium, or $R_1Mg$-halogen, where $R_1$ is alkyl of one to four carbons, for example methyl-magnesium bromide, ethyl-magnesium iodide, to give a tertiary alcohol [formula I, $R_1$ is alkyl (1–4 C), $R_2$ is H, $R_3$ is OH]. The hydroxy group ($R_3$) is optionally further etherified or esterified.

FLOW DIAGRAM

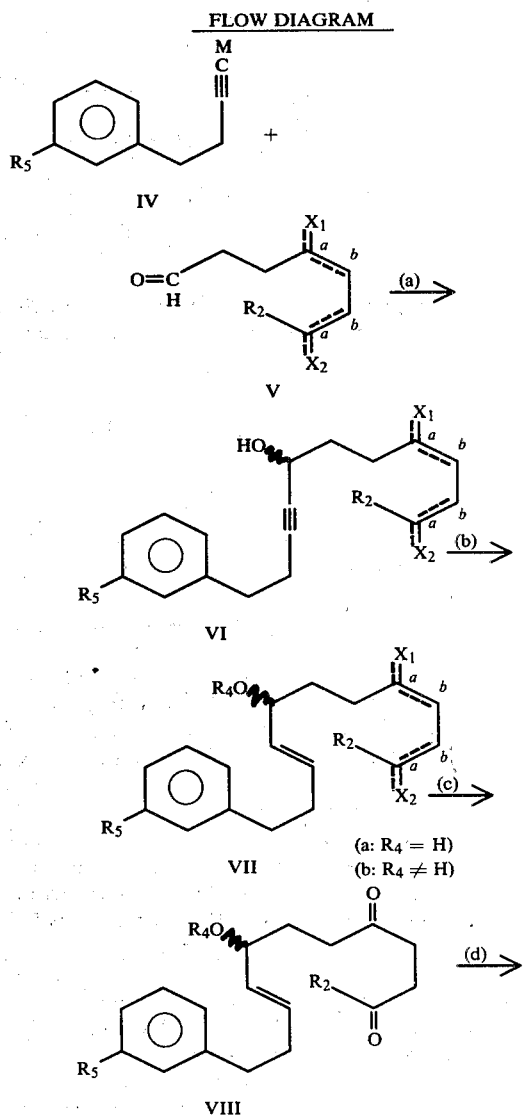

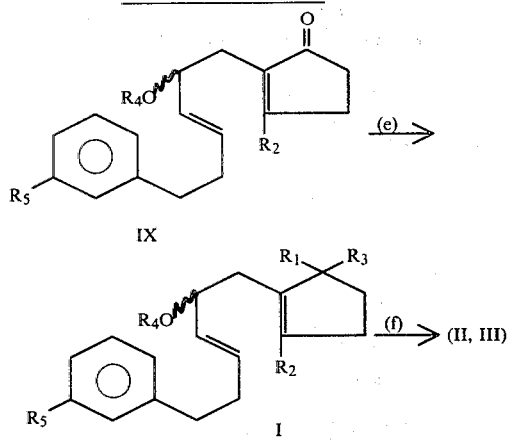

In the Flow Diagram $R_1$, $R_2$, $R_3$, $R_4$ and $R_5$ have the meanings assigned above. M is lithium or an Mg-halogen radical, for example MgBr; the bonds designated with "a" and "b" represent single or double bonds, with the proviso that when "a" represents a single bond, "b" is a double bond and vice-versa; $X_1$ and $X_2$ together form an epoxy group when "a" represents a single bond; if "a" is a double bond, when $X_1$ and $X_2$ each represent a suitable alkylene-dichalcogen group, that is, alkylenedioxy or alkylenedithio with 2–3 carbon atoms, for example ethylene-dioxy, propylene-dithio, ethylene-dithio.

The acetylide (IV) may be prepared by allowing a precursor 4-(m-$R_5$-phenyl)-butyne to react with alkyl-lithium, for example ethyl-lithium, or with magnesium shavings in the presence of an alkyl halide, for example methyl bromide or ethyl bromide, in an inert solvent, for example tetrahydrofuran at conditions well known to those in the art.

Examples of the aldehyde (V) are 7-$R_2$-4,7-bis-propylene-dithioheptanal, 7-$R_2$-4,7-bis-ethylene-dioxyheptanal, 3-(5'-$R_2$-2'-furyl)-propanal, 7-$R_2$-4,7-bis-ethylenedithio-heptanal.

The reduction of the propargyl alcohol (VI) to the alkyl alcohol (VII) with the desired (E)-configuration may be achieved with a metal hydride, for example lithium aluminium hydride.

The cyclisation substrate (I) obtained is cyclised with a Lewis acid under conditions specified below to give a tetracyclic compound with an axial $R_4O$-substituent.

The following comments can be made with reference to the substituents $R_1$ to $R_6$ inclusive:

Either $R_1$ or $R_2$ is usually methyl or ethyl, preferably methyl, while the other substituent is H. $R_3$ as a suitable "leaving" group known to those skilled in the art is usually alkoxy of one to four carbons, for example methoxy; otherwise (1) alkoxyalkoxy of two to four carbons, for example methoxymethoxy or 1'-ethoxyethoxy; (2) carboxyacyloxy of one to seven carbons, for example acetoxy, propionyloxy, butyroxy, pivaloyloxy, valeryloxy, benzoyloxy or (3) trimethylsilyloxy of less than fifteen carbons, for example, trimethylsilyloxy.

$R_4$ is hydrogen, a hydrocarbyl (hydrocarbon) group of one to fourteen carbons or carboxyacyl group of two to twelve carbons, or an unsubstituted heterocyclic of five to seven members and four to six carbons. Examples of hydrocarbyl groups are (1) alkyl, such as methyl or ethyl; (2) aryl such as phenyl or tolyl; (3) aralkyl such as benzyl, p-phenyl-benzyl, naphthylmethyl; or (4) cyclo-alkyl such as cyclopentyl or cyclohexyl. Examples of carboxyacyl-groups are acetyl, benzoyl, pivaloyl, decanoyl. An example of a trialkylsilyl group is trimethylsilyl. A preferable heterocyclic group is tetrahydropyranyl. Examples of suitable heterocyclic groups are the following unsubstituted heterocyclis: pyrrole, furan, thiophene, imidazole, oxazole, thiazole, pyrazole, pyrrolidine, pyridine, pyrimidine, and purine.

If the allyl alcohol (VII) is hydrolysed [step (c)] and cyclodehydrated [step (d)] without first protecting the hydroxy or equivalent group in the "pro-$C_{11}$" position, then allowance must be made for the possibility that the "pro-$C_{11}$" OH groups can be modified during these reactions. Hydrolysis of the furyl ring ($X_1$ and $X_2$ are epoxy) with methanol/sulphuric acid leads for example to a dioxo compound (VIII) with $R_4$ is $CH_3$. This does not necessarily constitute a drawback, but the reaction conditions are generally not optimal for a good yield. If a certain substituent $R_4O$ is desired in the cyclisation substrate (I), then it is better first to modify the "pro-$C_{11}$" hydroxy group in the compound (VII), for example by converting it into a benzyloxy group with benzylchloride/KOH in tetrahydrofuran, or into a methoxy group with $CH_3I/NaH$ in dimethyl sulphoxide, after which the hydrolysis and cyclodehydration can be performed.

The hydrolysis may be performed with acid, for example with $H_2SO_4$ in methanol or with $H_2SO_4$/HOAc or with $CH_3I/CH_3CN/H_2O$ under conditions known to those in the art. The cyclodehydration is achieved with alcoholic alkali, for example with KOH in ethanol or with trimethylbenzylammonium hydroxide.

It will be recognized by those skilled in the art that $R_4$ may optionally be modified after each of the reaction steps (c), (d) and (e).

The $R_5$'s ($R_{5(1)}$ and $R_{5(2)}$) each are preferably hydroxy, or in the alternative, optionally esterified or etherified hydroxy of less than fifteen carbons, for example (1) hydrocarbyloxy of one to eight carbons such as methoxy, ethoxy, cyclopentoxy, cyclohexenyloxy, benzyloxy; (2) α-alkoxyalkoxy of two to four carbons, such as methoxymethoxy, 1'-ethoxyethoxy; (3) trimethylsilyloxy or tetrahydropyranyloxy, and (4) carboxyacyloxy (1–7 C), such as acetoxy, privaloyloxy or benzoyloxy.

If $R_5$ is an oxy-group, then the positions 2, 4 and 6 of the phenyl nucleus are activated in the cyclisation. Due to steric factors, position 4 takes no part in the reaction and two products may therefore be formed as indicated above by the formulae (II) and (III). As previously noted, the ratio of formation of these two products can be changed considerably by a suitable choice of $R_4$ and $R_5$.

If for example, $R_4$ is methyl and $R_5$ is methoxy or trimethyl-silyloxy, then much more "para" product is formed than "ortho" product, the proportions of the two products being about 3:1 by weight. If $R_4$ is benzyl or pivaloyl, the ratio becomes much more favourable (10:1 or more) with respect to the "para" product, which is of importance since the "para" product leads to the desirable natural steroids.

If use is made as starting material of a butyne (IV) with $R_5$ being a protected hydroxy group, then the protective group may be retained during the various reaction steps, but it may also be modified. For some reaction steps, certain protective groups are preferred, while for other reaction steps yet other protective groups are preferred. For example, in the steps (a) and (b), $R_5$ is preferably methoxy or methoxy-methoxy. In the steps (c), (d) and (e), $R_5$ may optionally be hydroxy while in the cyclisation step, $R_5$ is preferably a "bulky"-group, if the "para"-product is of primary interest.

One permissible variation in the preparation of the cyclisation substrate is that the order of the (1) reduction of the propargyl alcohol and (2) the hydrolysis and (cyclo-dehydration) may be reversed. After the condensation of (IV) with (V), the hydrolysis and cyclo-dehydration are first performed to give 2-[2'-hydroxy-6'-(m-$R_5$-phenyl)-hex-3'-ynyl]-3-$R_2$-cyclopent-2-enone, after which the oxo group in the cyclopentenone is temporarily protected, for example in the form of the thioketal, the hexynyl group is reduced to the (E)-hexenyl group, and the oxo group is deprotected, giving compound IX. The deprotection of the oxo group may, optionally, be preceded by modification of the $R_4O$ substituent, for example conversion of the OH into benzyloxy.

The cyclisation substrate contains two asymmetric centers, namely, the carbon atom carrying the substituent $R_1$ and the carbon atom carrying the substituent $R_4O$. The stereochemistry of the cyclisation product proves to be governed predominantly by the latter center. In the cyclisation product, the substituent $R_4O$ has surprisingly been shown to occur predominantly in the axial configuration. If use is made as starting material of a racemic cyclisation substrate, i.e. a product with equal amounts of the (R)-$R_4O$- substituted and the (S)-$R_4O$-substituted compound, then a racemic tetracyclic product is formed, consisting of two enantiomers, while on grounds of the two asymmetric centers, four stereo-isomers would be formed in equal amounts if there were no optical induction. It is concluded that the asymmetric center with the substituent $R_1$ has little or no influence on the stereochemistry of the end product because the (S)-$R_1$-(S)-$R_4O$-substituted cyclisation substrate gives the same $R_4O$-axially substituted cyclisation product as the (R)-$R_1$-(S)-$R_4O$-substituted cyclisation substrate. For example, both 1(S)-3-methyl-2-[2'(S)-benzyloxy-6'-(m-methoxyphenyl)-3'(E)-hexenyl]-2-cyclopentenol and 1(R)-3-methyl-2-[2'(S)-benzyloxy-6'(m-methoxyphenyl)-3'(E)-hexenyl]-2-cyclopentenol give the "natural" 3-methoxy-11β-benzyloxy-$\Delta^{1,3,5(10),13(17)}$-gonatetraene of formula II on cyclisation.

It has been indicated in formula I that the substituent $R_4O$ may be present in the (R)-configuration or in the (S)-configuration. If use is made of the racemate as starting material, and the ortho/para isomerism of the aromatic ring is ignored, the cyclisation results in a racemate of the $R_4$-O-axially-substituted steroid compound with formula III. If an optically active cyclisation substrate is used as starting material, for example the (S)-methoxy compound, than an optically active compound of formula II is formed, that is, a "natural" 11β-methoxy-$\Delta^{1,3,5(10),13(17)}$-gonatetraene.

By epoxidising the 13(17)-olefine (II, III) obtained with a per-acid (for example m-chloroperbenzoic acid) the corresponding 13α,17α-epoxy compound below (formula X) is formed. Opening of the epoxide ring under weakly acid conditions, preferably by use of an aprotic Lewis acid, for example $BF_3$/diethyl ether, initiates a migration of the substituent $R_7$ from position 17 to position 13, whereby the corresponding 13β-$R_7$-17-ketone (XI) is formed from the α-epoxide (see Example III):

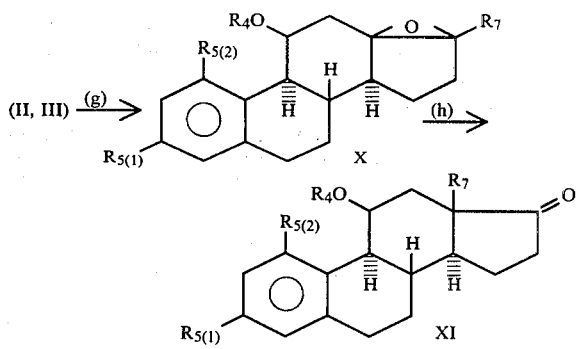

When $R_{5(1)}$ is methoxy and $R_7$ is methyl, the 3-methyl ether of 11β-methoxy-oestrone is obtained in this way.

In a corresponding fashion, the antipode can be converted into the ent-3-$R_5$-11β-$OR_4$-13β-$R_7$-$\Delta^{1,3,5(10)}$-gonatrien-17-one.

The internal condensation of the dioxo compound VIII (step (d)) may be brought about in the usual way, for example with alkaline ethanol or with trimethylbenzyl-ammonium hydroxide.

In the cyclisation Reaction (step e), an effective amount of an aprotic or a protic Lewis acid is used and the reaction is performed in a non-nucleophilic protic or aprotic solvent. Examples of suitable solvents are formic acid, acetic acid, trifluoro-acetic acid, trifluoro-ethanol, benzene, saturated hydrocarbons such as pentane, hexane, cyclohexane, and halogenated hydrocarbons such as dichloromethane.

Examples of protic Lewis acids are carboxylic acids with a pK (20° C.) of less than about 4, and preferably less than about 2, such as, for example, trifluoro-acetic acid, trichloro-acetic acid, formic acid.

Examples of aprotic Lewis acids are stannic chloride, titanium tetrachloride, zinc chloride, zinc bromide, boron trifluoride. Aprotic Lewis acids are preferably used, in an amount of about 0.1 to about 10 moles per mol cyclisation substrate, and preferably about 0.5 to about 5 moles per mol. Stannic chloride is preferable.

The cyclisation reaction is usually carried out at a temperature below room temperature (about 20°-22° C.) and above −150° C., preferably at a temperature between about +10° C. and about −100° C.

The mixtures of "ortho"- and "para"-products ("ortho" means A-aromatic steroid substituted in position 1, "para" means A-aromatic steroid substituted in position 3) of compound II–III obtained in the cyclisation step (e) may be separated in the usual way known to those in the art, for example by chromatography or by crystallization. Racemates of intermediate or final products may be resolved to give the optical antipodes in the usual way.

As to the reaction steps (a)—(f) the following additional information can be given:

Reaction step (a) is usually carried out at a temperature between about −100° C. and about 0° C., preferably between about −75° C. and about −25° C. The solvent is usually an etheric solvent, such as diethyl ether, tetrahydrofuran and mixtures thereof. A preferred solvent is an 1:1 mixture of diethyl ether and tetrahydrofuran.

Reaction step (b) is usually carried out at a temperature between about 30° C. and 70° C. preferably between 40° C. and 60° C. The solvent is an etheric solvent, such as tetrahydrofuran, dioxane or diethyl ether.

A preferred solvent is tetrahydrofuran. (cf. J.Org.Chem. 39, 968(1974)).

Reaction step (c) is usually carried out at a temperature between about 20° C. and 80° C., preferably between about 50° C. and 60° C. The solvent may be an etheric solvent, such as dimethoxyethane, or a mixture of water and an alcohol, such as ethanol. An 1:2 mixture of water and ethanol containing between 5 and 10 mmol HCl per liter, is very suited.

Reaction step (d) is usually carried out between about 60° C. and 80° C., preferably at about 80° C. The solvent is the same as used in step (c). An 1:2 mixture of water and ethanol containing between 5 and 10 mmol NaOH or an equivalent amount of KOH or trimethylbenzyl-ammoniumhydroxide is very suited.

Reaction step (e): The reduction of the ketone to an alcohol is carried out with a complex metallic hydride, such as lithiumaluminiumhydride, di-isobutylaluminium-hydride, sodium-di-isobutylboronhydride, at a temperature between about −50° C. and 0° C., preferably between about −25° C. and 0° C. The reaction of the ketone with a compound $R_1Li$ or $R_1Mg$halogen is usually carried out at a temperature between −70° C. and 0° C., preferably between −70° C. and −20° C. The solvent is usually an etheric solvent, preferably diethyl ether.

The reaction steps (a), (e), and (f) are preferably carried out in an inert atmosphere (nitrogen or argon blanket).

Cyclisation reaction step (f): When using a protic solvent, preferably a protic Lewis acid is used. A protic solvent, such as formic acid, trifluoro-acetic acid, trifluoro-ethanol, may also serve as protic Lewis acid. An aprotic solvent may be combined with either a protic Lewis acid or an aprotic Lewis acid.

Although the invention has been described with reference to the specific embodiments above numerous variations and modifications will become evident to those skilled in the art, without departing from the scope and spirit of the invention as described above, defined in the appended claims, and as shown in the following Examples:

EXAMPLE I (a) Preparation of 4,7-bis-(propylene-dithio)heptanal ethylene acetal (precursor of Compound V)

About 160 ml of a 2 N solution of butyl-lithium in hexane was added dropwise over a period of about 10 minutes to a solution of 41.80 g (157 mmol) 2,2'-ethylene-bis-(m-dithiane) in 1000 ml tetrahydrofuran at about −40° C. under nitrogen. The mixture was stirred at a temperature between about −20° C. and about −30° C. for about 4 hours. A solution of 28.8 g (160 mmol) 3-bromo-propanal ethylene acetal in 120 ml tetrahydrofuran was then added dropwise to the orange-colored solution over a period of about 30 minutes. The whole was stirred for 2 hours at about −20° C. and another 16 or so hours at room temperature (20°-25° C.). 40 ml water was slowly added dropwise at about 0° C. The volume was reduced to about 100 ml of evaporation under reduced pressure, the mixture was diluted with 500 ml water and extracted with methylene chloride. The combined organic layers were washed with water until neutral. After drying over sodium sulphate and filtering, the filtrate was evaporated to dryness under reduced pressure. The residue (59.0 g) was filtered through about 120 g neutral washed aluminium oxide with 500 ml toluene. After removal of toluene by evaporation, 39.0 g product was obtained.

(b) Preparation of 4,7-bis-(propylene-dithio)-heptanal (formula V, $R_2=H$, $X_1=X_2=$propylene-dithio)

250 ml 0.5 N hydrochloric acid was added with stirring to a solution of 25.62 g (70 mmol) 4,7-bis-(propylene-dithio)-heptanal ethylene acetal in 25 ml methylene chloride under nitrogen. The mixture was stirred in an oil bath at about 110° C. for about 5 hours. After cooling to room temperature, the mixture was extracted with methylene chloride. The organic layers were washed with water until neutral. After drying over sodium sulphate and filtering, the filtrate was evaporated to dryness under reduced pressure. The product obtained (22.5 g) was used immediately in the following step.

(c) Step (a): Preparation of dl-1-(m-methoxyphenyl)-8,11-bis-(propylene-dithio)-3-undecyn-5-ol (formula VI, $R_2=H$, $R_5=$methoxy, $X_1=X_2=$propylene-dithio)

A solution of 8.76 g (80 mmol) ethyl bromide in about 40 ml tetrahydrofuran was added dropwise over a period of about 1 hour to 1.92 g (80 mmol) magnesium shavings in 30 ml tetrahydrofuran under nitrogen. The whole was stirred for another 15 minutes or so, giving a clear solution to which was added dropwise over a period of about 30 minutes a solution of 12.8 g (80 mmol) 4-(m-methoxyphenyl)-1-butyne in about 20 ml tetrahydrofuran. The reaction mixture was then stirred at about 50° C. for about 1½ hours. After cooling to 5° C., a solution of 22.50 g (70 mmol) 4,7-bis(propylene-dithio)-heptanal in 50 ml tetrahydrofuran was added dropwise over a 20 minute period and the whole was stirred at room temperature for about 2 hours. After 30 ml of 6 N hydrochloric acid was then added at about 0° C. and the whole was evaporated to a bulk of about 50 ml under reduced pressure. The mixture was diluted with about 200 ml water and extracted with methylene chloride. The organic layers were washed with water until neutral. After drying over sodium sulphate and filtering, the filtrate was evaporated to dryness under reduced pressure. The residue was filtered through 150 g silica gel with 1 liter hexane/acetone 9:1 and gave 26.3 g product.

(d) Step (b): Preparation of dl-(E)-1-(m-methoxyphenyl)-8,11-bis-(propylene-dithio)-3-undecen-5-ol (formula VIIa, $R_2=H$, $R_5=$methoxy, $X_1=X_2=$propylene-dithio)

A solution of 8.20 g (17 mmol) dl-1-(m-methoxyphenyl)-8,11-bis-(propylene-dithio)-3-undecyn-5-ol in 40 ml tetrahydrofuran was added dropwise over a period of approximately 20 minutes to a suspension of 1.26 g (33 mmol) lithium aluminium hydride in 72 ml tetrahydrofuran under nitrogen, and the whole was then stirred in a waterbath at about 60° C. for about 3 hours. After cooling to about 0° C., the following consecutive additions were cautiously made dropwise to the suspension: 1.26 ml water, 1.26 ml 15% sodium hydroxide solution and about 3.5 ml water. Sodium sulphate (5 g) was added and the whole was filtered. The filtrate was evaporated to dryness under reduced pressure. Yield 8.20 g product.

(e) dl-(E)-1-(m-methoxyphenyl)-8,11-bis-(propylene-dithio)-3-undecen-5-ol, 5-benzyl ether (formula VIIb, $R_2=H$, $R_5=$methoxy, $X_1=X_2=$propylene-dithio, $R_4=$benzyl)

16.0 g (296 mmol) powered potassium hydroxide and 16.0 ml (171 mmol) benzyl chloride were added consecutively to a solution of 8.20 g (17 mmol) dl-(E)-1-(m-methoxyphenyl)-8,11-bis-(propylene-dithio)-3-undecen-5-ol in about 82 ml tetrahydrofuran under nitrogen, and the resultant mixture was stirred at room temperature for about 16 hours. After filtering, the filtrate was evaporated to dryness under vacuum. The residue was filtered through 100 g silica gel with toluene/ethylacetate 98:2 (600 ml), giving 8.78 g product.

(f) dl-2-[(E)-6-(m-methoxyphenyl)-2-benzyloxy-3-hexenyl]-2-cyclopentenone (Step (c)+Step (d)). (formula IX, $R_2=H$, $R_4=$benzyl, $R_5=$methoxy)

13.00 g (130 mmol) calcium carbonate was added under nitrogen to a solution of 5.65 g (9.84 mmol) dl-(E)-1-(m-methoxyphenyl)-8,11-bis-(propylene-dithio)-3-undecen-5-ol-5-benzyl ether in about 110 ml methyl cyanide-water 4:1. About 25 ml (400 mmol) methyl iodide was then added dropwise during a period of about 30 minutes, and the whole was stirred for a further about 5 hours in a water-bath at about 50° C. After filtering, the filtrate was poured into 400 ml water and extracted with methylene chloride. The methylene chloride layer was evaporated to dryness under reduced pressure. The residue was filtered through about 50 g silica gel with toluene/ethyl acetate (about 200 ml). The product (2.55 g) obtained by evaporation to dryness under reduced pressure, was stirred in about 250 ml 0.1 N ethanolic potassium hydroxide solution in an oil bath at about 80° C. for 2 hours. After cooling, the reaction mixture was poured into about 500 ml water and extracted with methylene chloride. The methylene chloride layer was washed with water and evaporated to dryness under reduced pressure. The residue (2.40 g) was filtered through 50 g silica gel with 250 ml toluene/ethyl acetate 9:1 giving 1.35 g product.

(g) Step (e): dl-1-methyl-2-[(E)-6-(m-methoxyphenyl)-2-benzyloxy-3-hexenyl]-2-cyclopentenol (formula I, $R_1=$methyl; $R_2=H$; $R_3=OH$; $R_4=$benzyl; $R_5=$methoxy)

6.0 ml 2 M methyl-lithium in ether was added dropwise at about 0° C. under nitrogen to a solution of 1.08 g (2.87 mmol) dl-2-[(E)-6-(m-methoxy-phenyl)-2-benzyloxy-3-hexenyl]-2-cyclopentenone of Step I(f) in about 40 ml absolute ether. The reaction mixture was stirred for a further about 30 minutes at about 0° C., poured into about 50 ml ice-water and extracted with ether. The ether layers were washed with water until neutral. After drying over sodium sulphate and filtering, the filtrate was evaporated to dryness under reduced pressure. Yield: 1.12 g product (oil). NMR (in $CDCl_3+C_5D_5N$): $\delta$1.25 and 1.29 (s, $CH_3$ at C-1), 3.78 (s, $CH_3O$), 3.9 (m, H—C—O), 4.20 and 4.50 (2×d, J=12, $ArCH_2O$), 5.15–5.85 (m, olefinic protons).

EXAMPLE II

Cyclisation (step (f));
dl-3-methoxy-11β-benzyloxy-17-methyl-$\Delta^{1,3,5(10),13(17)}$-gonatetraene (formula II, $R_5$=methoxy; $R_4$=benzyl $R_7$=methyl)

A solution of 1.12 g dl-1-methyl-2-[(E)-6-(m-methoxyphenyl)-2-benzyloxy-3-hexenyl]-2-cyclopentenol of Example I in 2 ml methylene chloride was added dropwise over a 30 minute period to a solution of 1.02 ml (9.0 mmol) stannic chloride in 30 ml methylene chloride at about −75° C. under a nitrogen atmosphere. The whole was stirred for a further about 45 minutes at about −75° C., after which 30 ml of about 20% methanolic potassium hydroxide solution was added dropwise to the reaction mixture over a period of about 15 minutes. The reaction mixture was poured into 100 ml water and extracted with methylene chloride. The methylene chloride layers were washed with water until neutral and evaporated to dryness under reduced pressure. The residue (1.05 g) was chromatographed on 30 g silica gel with toluene/ethyl acetate 99:1, giving 0.52 g product in the form of an oil. NMR (in $CDCl_3$): δ1.60 (s, 17—$CH_3$), 3.76 (s, $CH_3O$), 4.15–4.5 (m, 11α-H+ArC-$H_2O$).

EXAMPLE III

Preparation of
dl-3-methoxy-11β-benzyloxy-$\Delta^{1,3,5(10)}$-oestratrien-17-one (Step (g)+Step (h)). (formula XI, $R_4$=benzyl, $R_5$=methoxy, $R_7$=methyl)

A solution of 173 mg m-chloro-perbenzoic acid (content 70%, 0.70 mmol) in 10 ml methylene chloride was added dropwise at 0° C. to a solution of 187 mg (0.50 mmol) dl-3-methoxy-11β-benzyloxy-17-methyl-$\Delta^{1,3,5(10),13(17)}$-gonatetraene in 20 ml methylene chloride and the resultant mixture was stirred for a further about 2.5 hours at about 0° C.

The reaction mixture was vigorously stirred with 12.5 ml saturated sodium bicarbonate solution for about 15 minutes. The organic layer was separated and dried over anhydrous potassium carbonate. The solution, containing the 13α,17α-epoxide, was filtered and mixed with 1 ml boron trifluoride ethereate. After shaking vigorously for 1 minute, the red reaction mixture was washed with 25 ml 10% potassium carbonate solution. The organic layer was separated and dried over anhydrous potassium carbonate. Evaporation to dryness yielded 190 mg residue, which was purified by chromatography on 10 g silica gel with hexane/ethyl acetate 9:1, followed by 8:2. In this way, 90 mg of pure product was obtained; oil, NMR (in $CDCl_3$): δ1.12 (s, 13—$CH_3$), 3.73 (s, $CH_3O$), 4.35 (q, 11α-H), 4.30 and 4.60 (2×d, J=$ArCH_2O$).

EXAMPLE IV (a) Preparation of
dl-(E)-1-(m-methoxyphenyl)-8,11-bis-(1,3-propylene-dithio)-3-undecen-5-ol, 5-methyl ether (formula VIIb, $R_2$=H, $R_4$=methyl, $R_5$=methoxy, $X_1$=$X_2$=propylene-dithio)

1.00 g (20.8 mmol) sodium hydride (50% suspension in oil was added under nitrogen to a solution of 4.24 g (8.7 mmol) dl-(E)-1-m-methoxyphenyl)-8,11-bis-(propylene dithio)-3-undecen5-ol in about 15 ml tetrahydrofuran and 50 ml dimethyl sulphoxide. After stirring for about 5 minutes at room temperature 1.00 ml (15.5 mmol) methyl iodide was added. The reaction mixture was stirred for a further about 60 minutes at room temperature after which it was poured into 500 ml ice-water and extracted with methylene chloride. The methylene chloride layers were washed with water. After drying over sodium sulphate, the methylene chloride solution was evaporated to dryness under reduced pressure. Yield: 4.5 g product.

(b)
dl-2-[(E)-6'-m-methoxyphenyl)-2'-methoxy-3'-hexenyl]-2-cyclopentenone (Step (c)+Step (d))

In an exact way analogous to that described in example I(f), 4.5 g dl-(E)-1-(m-methoxyphenyl)-8,11-bis-(1,3-propylene-dithio)-3-undecen-5-ol 5-methyl ether was converted into 0.4 g product.

(c)
dl-1-methyl-2-[(E)-6'-(m-methoxyphenyl)-2'-methoxy-3'-hexenyl]-2-cyclopentenol (Step (e)). (formula I, $R_1$=methyl, $R_2$=H, $R_3$=OH, $R_4$=methyl, $R_5$=methoxy)

In an exact way analogous to that described in example I(g), 0.4 g dl-(E)-1-(m-methoxyphenyl)-8,11-bis-(1,3-propylene-dithio)-3-undecen-5-ol 5-methyl ether was converted into 0.4 g product (oil). NMR (in $CDCl_3$+$C_5D_5N$): δ1.25 and 1.29 (s, $CH_3$ at C-1), 3.16 (s, aliphatic $CH_3O$), 3.75 (s, aromatic $CH_3O$), 3.65 (m, H—C—$OCH_3$), 5.1–5.8 (m, olefinic protons).

EXAMPLE V

Cyclisation. Preparation of dl-3,
11β-dimethoxy-17-methyl-$\Delta^{1,3,5(10),13(17)}$-gonatetraene (Step (f)). (formula II, $R_4$=methyl, $R_5$=methoxy, $R_7$=methyl)

In an exact way analogous to that described in example II, 0.4 g dl-1-methyl-2-[(E)-6'-(m-methoxyphenyl)-2'-methoxy-3'-hexenyl]-2-cyclopentenol was cyclised to 0.2 g product (oil). NMR (in $CDCl_3$): δ1.62 (s, 17—$CH_3$), 3.20 (s, 11β—$OCH_3$), 3.75 (3—$OCH_3$), 4.15 (q, 11α—H).

EXAMPLE VI (a)
dl-3-methyl-2-[6-(m-methoxyphenyl)-2-hydroxy-3-hexynyl]-2-cyclopentenone A solution of 10.00 g (33.6 mmol) dl-1-(m-methoxyphenyl)-7-(5-methyl-2-furyl)-3-heptyn-5-ol in 20 ml acetic acid, about 10 ml water and 0.40 ml about 20% sulphuric acid was stirred under nitrogen in an oil-bath at 90° C. for about 24 hours. After cooling, the mixture was poured into 200 ml water and extracted with methylene chloride. The methylene chloride layer was washed with water and evaporated to dryness under reduced pressure. The residue (10.60 g) was dissolved in 500 ml of about 0.1 N ethanolic potassium hydroxide solution and stirred under nitrogen in an oil-bath at about 80° C. for about 1 hour. After cooling, the mixture was poured into 1000 ml water and extracted with methylene chloride. The methylene chloride layer was washed with water and evaporated to dryness under reduced pressure. Yield: 9.85 g.

(b)

dl-3-methyl-2[6-(m-methoxyphenyl)-2-hydroxy-3-hexynyl]-2-cyclopentenone ethylene dithioketal A solution of about 9.85 g (33 mmol) dl-3-methyl-2-[6-(m-methoxyphenyl)-2-hydroxy-3-hexynyl]-2-cyclopentenone in about 50 ml methanol, about 1.50 ml boron trifluoride etherate and about 5.0 ml ethanedithiol was refluxed under nitrogen for about 3 hours. After cooling, the reaction mixture was poured into about 500 ml water and extracted with methylene chloride. The methylene chloride layer was washed with water and evaporated to dryness under reduced pressure. The residue was filtered through 130 g neutral washed aluminium oxide with hexane/methylene chloride 9:1 (700 ml), giving 9.20 g product.

(c)

dl-3-methyl-2-[(E)-6-(m-methoxyphenyl)-2-benzyloxy-3-hexenyl]-2-cyclopentenone ethylene dithioketal A solution of about 9.20 g (24.6 mmol) dl-3-methyl-2-[6-(m-methoxy-phenyl)-2-hydroxy-3-hexynyl]-2-cyclopentenone ethylene dithioketal in 53 ml tetrahydrofuran was added dropwise over a period of about 20 minutes to a suspension of 1.86 g (49 mmol) lithium aluminium hydride in about 80 ml tetrahydrofuran under a nitrogen atmosphere. The mixture was stirred in a water-bath at about 60° C. for about 4 hours. After cooling to about 0° C., the following consecutive dropwise additions were cautiously made to the suspension: 1.86 ml water, 1.86 ml 15% sodium hydroxide solution and 5.50 ml water. Sodium sulphate (5 g) was added and the whole was filtered. The filtrate was evaporated to dryness under reduced pressure and the residue (7.35 g) was dissolved in about 100 ml tetrahydrofuran. The following consecutive additions were made to this solution under nitrogen: 20.0 g (370 mmol) powdered potassium hydroxide and 20.0 ml (214 mmol) benzyl chloride. The whole was then stirred for about 16 hours at room temperature. After filtering, the filtrate was evaporated to dryness under reduced pressure. The residue was filtered through about 100 g silica gel with hexane-/acetone 9:1 by weight (500 ml) giving 8.70 g product.

(d)

dl-3-methyl-2-[(E)-6-(m-methoxyphenyl)-2-benzyloxy-3-hexenyl]-2-cyclopentenone (formula IX, $R_2=CH_3$; $R_4$=benzyl; $R_5$=methoxy)

About 10.0 (100 ml) calcium carbonate was added under nitrogen to a solution of 8.70 g (18.6 mmol) dl-3-methyl-2[(E)-6-(m-methoxyphenyl)-2-benzyloxy-3-hexenyl]-2-cyclopentenone ethylene dithioketal in about 100 ml methyl cyanide/water 4:1 by weight. About 12.5 ml (200 mmol) methyl iodide was then added dropwise with vigorous stirring during a period of about 1 hour and the whole was stirred for a further about 5 hours in a water-bath at about 50° C. After filtering, the filtrate was poured into about 500 ml water and extracted with methylene chloride. The methylene chloride layer was washed with water and evaporated to dryness under reduced pressure. The residue was filtered through 90 g silica gel with hexane/ethyl acetate 95:5 by weight (500 ml), giving 3.60 g product.

(e)

dl-3-methoxy-11β-benzyloxy-17-methyl-$\Delta^{1,3,5(10),13(17)}$-gonatetraene (formula II, $R_4$=benzyl, $R_5$=methoxy, $R_7$=methyl)

A solution of dl-3-methyl-2-[(E)-6-(m-methoxyphenyl)-2-benzyloxy-3-hexenyl]-2-cyclopentenone (1.50 g, 3.86 mmol) in 15 ml ether was added dropwise over a period of about 15 minutes to a suspension of 0.37 g (9.7 mmol) lithium aluminium hydride in about 30 ml ether at about −5° C. under nitrogen. The mixture was stirred for a further about 30 minutes at about 0° C. The following consecutive dropwise additions were then cautiously made: about 0.37 ml water, 0.37 ml 15% sodium hydroxide solution and about 1.10 ml water. Sodium sulphate (1 g) was added and the suspension was filtered. The filtrate was evaporated to dryness under reduced pressure. The residue (1.50 g) was dissolved in 4.5 ml methylene chloride and added dropwise over a period of 30 minutes to a solution of 1.36 ml (12 mmol) stannic chloride in 13 ml methylene chloride at about −75° C. under nitrogen. 20 ml 20% methanolic potassium hydroxide was then added dropwise to the reaction mixture during an approximate 15 minute period. The reaction mixture was poured into approximately 100 ml water and extracted with methylene chloride. The methylene chloride layers were washed with water and evaporated to dryness under reduced pressure. The residue (1.40 g) was chromatographed on 45 g silica gel with hexane/ethylacetate 95:5 (200 ml), giving 0.43 g product, which was identical with the product of Example II.

EXAMPLE VII dl-3-methoxy-11β-benzyloxy-17-ethyl-$\Delta^{1,3,5(10),13(17)}$-gonatetraene (formula II, $R_4$=benzyl; $R_5$=methoxy; $R_7$=ethyl)

Dl-2-[(E)-(m-methoxyphenyl-2-benzyloxy-3-hexenyl]-2-cyclopentone was converted with ethyl-lithium into dl-1-ethyl-2-[(E)-6-(m-methoxy-phenyl)-2-benzyloxy-3-hexenyl]-2-cyclopentenol in the exact way described in example I(g).

A solution of 0.30 g (0.74 mmol) dl-1-ethyl-2-[(E)-6-(m-methoxyphenyl)-2-benzyloxy-3-hexenyl]-2-cyclopentenol in 3 ml nitro-ethane was added dropwise over a period of about 10 minutes to a solution of 0.34 g (1.5 mmol) zinc bromide in 15 ml nitro-ethane at about −20° C. under nitrogen. The reaction mixture was stirred at about −20° C. for a further approximately 3 hours after which about 30 ml 10% sodium hydroxide solution was added. The reaction mixture was poured into 50 ml water and extracted with methylene chloride. The methylene chloride layer was washed with water and evaporated to dryness under reduced pressure. The residue was filtered through 9 g silica gel with hexane/ethyl acetate 95:5 (20 ml), giving 140 mg product, melting point 90°–92° C.

EXAMPLE VIII (a) 4,7-Bis-(ethylene-dithio)-heptanoic acid n-propylester (precursor of compound V)

A solution of 12.0 g (80 mmol) of 3-(2-furyl)propionic acid, 20 ml (22.4 g., 0.24 mol) ethanedithiol and 20 ml borontrifluoride-etherate in 160 ml n-propanol was refluxed for about 22 hours. The reaction mixture was cooled, diluted with ether, and washed with 2 N sodiumhydroxide-solution. The organic layer was dried on waterfree potassium carbonate and evaporated to dryness. The residue was chromatographed through 400 g silica gel with hexane/ethylacetate 8:2, giving 22.5 g product (colorless oil).

(b) 4,7-Bis-(ethylene-dithio)-heptanal (Formula V, $R_2=H$; $X_1=X_2=$ ethylene-dithio)

A solution of the n-propylester of Example VIII(a) (21.1 g, 60 mmol) in 120 ml dry toluene was cooled to −78° C. under nitrogen. While stirring, 50 ml 1,2 M di-isobutylaluminiumhydride in toluene was added dropwise in about 30 minutes. Ten minutes later 10 ml water was added. The reaction mixture was brought to room temperature and filtered through hyflo. The filtrate was dried on waterfree sodium sulphate and evaporated to dryness. The residue was chromatographed through 200 g silica gel with hexane/ethylacetate 8:2, giving 13.4 g product (colorless oil).

(c) dl-1-(m-methoxyphenyl-8,11-bis-ethylene-dithio)-3-undecyn-5-ol (formula VI, $R_2=H$; $R_5=$methoxy; $X_1=X_2=$ethylenedithio)

A solution of 8.0 g (50 mmol) 4-(m-methoxyphenyl)-1-butyne was cooled to about 10° C. under nitrogen. A solution of n-butyl-lithium in hexane (1.6 M) was added dropwise until the color changed to a light yellow (about 33 ml). The solution thus obtained was stirred for about 30 minutes at about 0° C. and was subsequently cooled to about −15° C. A solution of 12.8 g (43.6 mmol) 4,7-bis-(ethylene-dithio)heptanal in 75 ml tetrahydrofuran was added slowly and the whole was then stirred for about 1 hour at about −10 C. The reaction mixture was poured into water and extracted with ether. The extracts were dried over anhydrous sodium sulphate and evaporated to dryness. The residue was chromatographed on 300 g silica gel with hexane/ethylacetate 8:1, giving about 17.6 g product.

(d) dl-(E)-1-(m-methoxyphenyl)-8,11-bis-(ethylenedithio)-3-undecen-5-ol (formula VIIa, $R_2=H$; $R_5=$methoxy; $X_1=X_2=$ethylene-dithio)

The compound obtained in example VIII(c) was reduced in an exact way analogous to that described in example I(d). The product was obtained as a colorless oil in quantitative yield.

(e) dl-(E)-1-(m-methoxyphenyl)-5-pivaloyloxy-8,11-bis-(ethylene-dithio)-3-undecene (formula VIIb, $R_2=H$, $R_5=$methoxy; $X_1=X_2=$ethylene-dithio; $R_4=$pivaloyl)

The compound obtained in example VIII(d) (18.2 g, 40 mmol) was dissolved in 200 ml dry pyridine. The solution was cooled under a nitrogen atmosphere to about 0° C., after which about 10 ml pivaloyl chloride (about 2 eq.) was added dropwise with stirring. The resultant mixture was stirred for about 2 hours at about 0° C. and subsequently for about 16 hours at room temperature, after which water was added and the whole was extracted with ether. The ether extracts were washed with 2 N hydrochloric acid, saturated sodium bicarbonate solution, and water, and finally dried over anhydrous about $MgSO_4$. The solvent was removed by evaporation and the residue was chromatographed on about 300 g silica gel with hexane/ethylacetate 9:1. 20.1 g product was obtained.

(f) dl-2-[(E)-6-(m-methoxyphenyl)-2-pivaloyloxy-3-hexenyl]-2-cyclopentenone (formula IX, $R_2=H$; $R_4=$pivaloyl; $R_5=$methoxy)

The compound obtained in example VIII(e) (4.3 g, 8 mmol) was hydrolysed in a way analogous to that described in example I(f). The crude product was purified by chromatography on 70 g silica gel with hexane/ethylacetate 8:2. The keto-aldehyde (1.74 g) obtained in this way was dissolved in 175 ml 96% ethanol and mixed with 1.75 ml 40% trimethylbenzyl-ammonium hydroxide ("Triton B"). The mixture was heated at 60° C. for 30 minutes, cooled, and further worked up as described in example I(f). In this way, 1.40 g product was obtained in the form of a light yellow oil.

(g) dl-1-methyl-2-[(E)-6-(m-methoxyphenyl)-2-pivaloyloxy-3-hexenyl]-2-cyclopentenol (formula I, $R_1=$methyl; $R_2=H$; $R_3=$OH; $R_4=$pivaloyl; $R_5=$methoxy)

The compound obtained in example VIII(f) (1.40 g, 3.8 mmol) was dissolved in about 70 ml dry ether. The solution was cooled under nitrogen to about −70° C. after which 1.9 ml 2 M methyl-lithium (3.8 mM) in ether was added dropwise. The reaction mixture was stirred for 30 minutes at about −70° C. and then poured into water. The organic layer was separated and dried over anhydrous sodium sulphate. Removal of solvent by evaporation gave 1.44 g product (oil). NMR (in $CDCl_3 + C_5D_5N$): $\delta 1.13$ (s, $t-C_4H_9COO$), 1.25 and 1.29 (s, $CH_3$ at C-1), 3.75 (s, $CH_3O$), 5.1–5.8 (m, olefinic protons + H—C—O).

EXAMPLE IX

Cyclisation dl-3-methoxy-11β-pivaloyloxy-17-methyl-$\Delta^{1,3,5(10),13(17)}$-gonatetraene (formula II, $R_5=$methoxy; $R_4=$pivaloyl; $R_7=$methyl)

The product from Example VIII(g) (1.44 g, 3.7 mmol) was cyclised in a way analogous to that described in Example II. The crude product was purified by chromatography on 40 g silica gel with hexane/ethylacetate 9:1. In this way, 0.69 g pure product was obtained, melting point 91°–92° C.

EXAMPLE X

Dl-3,11β-dihydroxy-$\Delta^{1,3,5(10)}$-estratriene-17-one-3-methylether

The product of Example IX (0.69 g, 1.9 mmol) was converted in the corresponding 13α,17α-epoxide in an exact way analogous to that described in Example III. The epoxide (m.p. 101°–105° C.) was treated with lithiumaluminiumhydride (0.07 g, 1.9 mmol) at −40° C. to convert the pivaloyloxy group into a hemi-acetal group. The product thus obtained (m.p. 152° C.) was reacted with borontrifluorideetherate in toluene, exactly as described in Example III. Chromatographic purification gave 0.20 g product, m.p. 95°–100° C.

EXAMPLE XI (a)

dl-(E)-1-(m-methoxyphenyl)-8,11-bis-(ethylenedithio)-3-undecen-5-ol-5-benzoate (formula VIIb, $R_2$=H; $R_5$=methoxy; $X_1$=$X_2$=ethylene-dithio; $R_4$=benzoyl)

In an exact way analogous to that described in Example VIII(e), 2.3 g dl-(E)-1-(m-methoxyphenyl)-8,11-bis-(ethylene-dithio)-3-undecen-5-ol was reacted with 1.3 ml benzoyl chloride to give the desired product (2.57 g).

(b)

dl-2-[(E)-6-(m-methoxyphenyl)-2-benzoyloxy-3-hexenyl]-2-cyclopentenone (formula IX, $R_2$=H; $R_4$=benzoyl; $R_5$=methoxy)

The product from Example XI(a) (2.57 g, 4.6 mmol) was stripped of the thioketal group in a way analogous to that described in example I(f). The resultant keto-aldehyde (1.0 g) was cyclodehydrated in an exact way analogous to that of Example VIII(f), giving 0.66 g of the desired product.

(c) dl-1-methyl-2-[(E)-6-(m-methoxyphenyl)-2-benzoyloxy-3-hexenyl]-2-cyclopentenol (formula I, $R_1$=methyl; $R_2$=H; $R_3$=OH; $R_4$=benzoyl; $R_5$=methoxy).

The product from Example XI(b) (0.66 g, 1.7 mmol) was converted into the desired product in quantitative yield in an exact way analogous to that of Example VIII(g). Oil, NMR (in $CDCl_3+C_5D_5N$): $\delta$1.32 (s, $CH_3$ at C-1), 3.78 (s, $CH_3O$), 5.3–6.0 (m, olefinic protons+H—C—O).

EXAMPLE XII dl-3-methoxy-11$\beta$-benzoyloxy-17-methyl-$\Delta^{1,3,5(10),13(17)}$-gonatetraene (formula II, $R_4$=benzoyl; $R_5$=methoxy; $R_7$=methyl)

The product from Example XI(c) (0.68 g, 1.67 mmol) was cyclised in a way analogous to that of Example II. The crude product was purified by chromatography on 20 g silica gel with hexane/ethylacetate 9:1, giving 169 mg pure product, melting point 133° C. (decomposition).

EXAMPLE XIII (a)

dl-(E)-1-(m-methoxyphenyl)-8,11-bis-(ethylenedithio)-3-undecen-5-ol-5-$\alpha$-naphthylmethyl ether (formula VIIb, $R_2$=H; $R_5$=methoxy, $X_1$=$X_2$=ethylene-dithio; $R_4$=$\alpha$-naphthylmethyl)

A solution of 2.3 g (5 mmol) dl-(E)-1-(m-methoxyphenyl)-8,11-bis-(ethylene-dithio)-3-undecen-5-ol in 10 ml dry tetrahydrofuran was mixed with 1 ml hexamethylphosphoric acid triamide and 0.48 g sodium hydride (50% suspension in mineral oil, 10 mmol). The mixture was heated at about 50° C. for about 30 minutes, after which 1.77 g (10 mmol) $\alpha$-chloromethyl-naphthalene was added dropwise. The mixture was stirred for about 4 hours at about 50° C., after which water and ether were added. The organic layer was separated, dried over anhydrous sodium sulphate and evaporated to dryness. The residue was chromatographed on 40 g silica gel with hexane/ethylacetate about 9:1 by weight. 2.58 g product was obtained in the form of a colorless oil.

(b)

dl-2-[(E)-6-(m-methoxyphenyl)-2-$\alpha$-naphthylmethyloxy)-3-hexenyl]-2-cyclopentenone (formula IX, $R_2$=H; $R_4$=$\alpha$-naphthylmethyl; $R_5$=methoxy)

The thioketal group in the product from Example XIII(a) (2.58 g, 4.3 mmol) was removed in an exact way analogous to that described in Example I(f). The resultant keto-aldehyde (1.06 g) was cyclo-dehydrated in a way analogous to that of Example VIII(f), giving 0.60 g pure product.

(c)

dl-1-methyl-2-[(E)-6-(m-methoxyphenyl-2-($\alpha$-naphthylmethyloxy)-3-hexenyl]-2-cyclopentenol (formula I, $R_1$=methyl; $R_2$=H; $R_3$=OH; $R_4$=$\alpha$-naphthylmethyl; $R_5$=methoxy)

The compound immediately preceding (0.60 g, 1.4 mmol) was converted into the desired product (0.63 g) in an exact way analogous to that of Example VIII(g). Oil, NMR (in $CDCl_3+C_5D_5N$): $\delta$1.15 and 1.22 (s, $CH_3$ at C-1), 3.66 (s, $CH_3O$), 3.92 (m, H—C—O), 4.75 (q, J=12, $ArCH_2O$), 5.2–5.8 (m, olefinic protons).

EXAMPLE XIV dl-3-methoxy-11$\beta$-$\alpha$-naphthylmethyloxy-17-methyl-$\Delta^{1,3,5(10),13(17)}$-gonatetraene (formula II, $R_4$=$\alpha$-naphthylmethyl; $R_5$=methoxy; $R_7$=methyl)

The product from Example XIII(c) (0.63 g, 1.4 mmol) was cyclised in an exact way analogous to that of Example II. The desired product was isolated by chromatography on silica gel with hexane/ethylacetate 9:1. Yield: 180 mg oil. NMR (in $CDCl_3$); $\delta$1.6 (s, 17—$CH_3$), 3.73 (s, $CH_3O$), 4.70 and 4.95 (2×d, J=12, $ArCH_2O$), 4.43 (q, J=2, 11$\alpha$H).

EXAMPLE XV dl-1-methyl-2-[(E)-6-(m-methoxyphenyl)-2-trimethylsilyloxy-3-hexenyl]-2-cyclopentenol (formula I, $R_1$=methyl; $R_2$=H; $R_3$=OH; $R_4$=trimethylsilyl; $R_5$=methoxy)

Starting from dl-(E)-1-(m-methoxyphenyl)-8,11-bis-(ethylene-dithio)-3-undecen-5-ol and trimethylsilyl chloride, the title cyclopentenol was prepared in an exact way analogous to that described in Example XIII.

EXAMPLE XVI dl-3-methoxy-11$\beta$-trimethylsilyloxy-17-methyl-$\Delta^{1,3,5(10),13(17)}$-gonatetraene (formula II, $R_4$=trimethylsilyl; $R_5$=methoxy; $R_7$=methyl)

The product from Example XV was cyclised to the title gonatetraene in an exact way analogous to that described in Example II.

EXAMPLE XVII dl-1-methyl-2[(E)-6-(m-methoxyphenyl)-2-(p-phenylbenzyloxy)-3-hexenyl]-2-cyclopentenol (formula I, $R_1$=methyl; $R_2$=H; $R_3$=OH; $R_4$=p-phenylbenzyl; $R_5$=methoxy)

Starting from dl-(E)-1-(m-methoxyphenyl)-8,11-bis-(ethylene-dithio)-3-undecen-5-ol and p-phenylbenzyl chloride, the title cyclopentenol was obtained in an exact way analogous to that described in Example XIII. Oil, NMR (in $CDCl_3+C_5D_5N$): $\delta$1.25 and 1.30 (s, $CH_3$ at C-1), 3.76 (s, $CH_3O$), 3.83 (m, H—C—O), 4.25 and 4.48 (2×d, J=12, ArCH₂O), 5.2–5.9 (m, olefinic protons).

EXAMPLE XVIII dl-3-methoxy-11β-p-phenylbenzyloxy-17-methyl-Δ$^{1,3,5(10),13(17)}$-gonatetraene (formula II, R₄=p-phenylbenzyl; R₅=methoxy; R₇=methyl)

The product from Example XVII was cyclised to the title gonatetraene in a way analogous to that of Example II. Oil, NMR (in CDCl₃): δ1.65 (s, 17-CH₃), 3.74 (s, CH₃O), 4.40 (q, J=2, 11αH), 4.40 and 4.56 (2×d, J=12, ArCH₂O).

It should be noted that the 11β-substituted 17-alkyl-Δ$^{1,3,5(10),13(17)}$-gonatetraenes obtained in the cyclisation and the 13α,17α-epoxy derivatives thereof are novel compounds. These compounds have hormonal properties and are furthermore of importance for the synthesis of known 11β-substituted steroids.

It is claimed as the invention:

1. A cyclisation substrate compound of the formula:

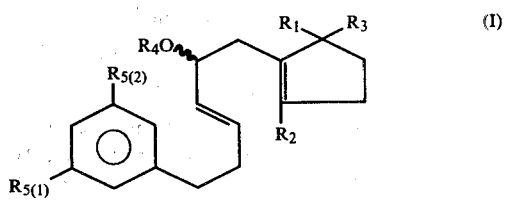

wherein:
(a) R₁ is H or alkyl of one to four carbons;
(b) R₂ is H or alkyl or one to four carbon atoms, with the proviso that R₁ is H when R₂ is alkyl, and with the proviso that R₂ is H when R₁ is alkyl;
(c) R₃ is a suitable leaving group selected from the group consisting of hydroxy, alkoxyalkoxy of two to four carbons, alkoxy of one to four carbons, acyloxy of one to about seven carbon atoms, and trialkylsilyloxy of less than fifteen carbons;
(d) R₄ is H and
(e) R₅(₁) and R₅(₂) are each H, alkyl of one to eight carbons, or optionally esterified or etherified hydroxy selected from the group consisting of hydroxy, alkoxy or one to four carbons, alkoxyalkoxy of two to four carbons, trialkylsilyloxy of one to fifteen carbons, cycloalkoxy of four to eight carbons carboxyacyloxy of one to seven carbons or heterocyclic ether of five to seven atoms and four to six carbons, with the proviso that at least one of R₅(₁) and R₅(₂) is hydrogen.

2. The compound of claim 1 wherein one of R₁ and R₂ is methyl or ethyl and the other is hydrogen.
3. The compound of claim 1 wherein R₃ is hydroxy.
4. The compound of claim 1 wherein one of R₅(₁) and R₅(₂) is methoxy.
5. The compound of claim 1 wherein R₁ is CH₃, R₂ is H, R₃ is OH, and one R₅(₁) and R₅(₂) is methoxy.
6. The compound of claim 1 wherein R₁ is methyl, R₂ is H, R₃ is OH, and one of R₅(₁) and R₅(₂) is methoxy.
7. The compound of claim 1 wherein R₁ is methyl, R₂ is H, R₃ is OH, and R₅ is methoxy.
8. The compound of claim 1 wherein R₁ is CH₃, R₂ is H, R₃ is hydroxy, and R₅ is methoxy.
9. The compound of claim 1 wherein R₁ is CH₃, R₂ is H, R₃ is OH, and R₅ is methoxy.
10. The compound of claim 1 wherein R₁ is CH₃, R₂ is H, R₃ is OH, and R₅ is methoxy.
11. The compound of claim 1 wherein R₁ is CH₃, R₂ is H, R₃ is OH, and R₅ is methoxy.
12. A compound of the formula:

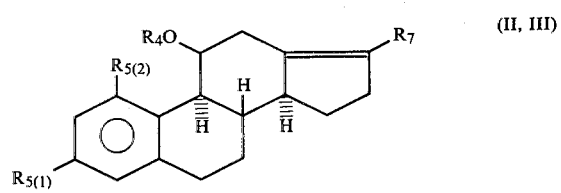

wherein:
(a) R₄ is H;
(b) R₅(₁) and R₅(₂) are each H, alkyl or one to eight carbons, or an optionally esterified or etherified hydroxy group selected from the group consisting of hydroxy, alkoxy of one to four carbons, alkoxyalkoxy of two to four carbons, trialkylsilyloxy of one to fifteen carbons, cycloalkoxy of four to eight carbons, carboxyacyloxy of one to seven carbons for heterocyclic ether of five to seven atoms and four to six carbons with the proviso that at least one of R₅(₁) and R₅(₂) is H; and
(c) R₇ is an alkyl of one to about four carbon atoms.
13. The compound of claim 12 wherein one of R₅(₁) and R₅(₂) is methoxy.
14. The compound of claim 12 wherein R₇ is CH₃ or ethyl.
15. The compound of claim 12 wherein one of R₅(₁) and R₅(₂) is methoxy and R₇ is methyl.
16. The compound of claim 12 wherein one of R₅(₁) and R₅(₂) is benzyl and R₆ is methyl.
17. The compound of claim 12 wherein one of R₅(₁) and R₅(₂) is methoxy and R₇ is ethyl.
18. The compound of claim 12 wherein one of R₅(₁) and R₅(₂) is methoxy and R₇ is methyl.
19. The compound of claim 12 wherein one of R₅(₁) and R₅(₂) is methoxy, and R₇ is methyl.
20. The compound of claim 12 wherein one of R₅(₁) and R₅(₂) is methoxy and R₇ is methyl.
21. The compound of claim 12 wherein one of R₅(₁) and R₅(₂) is methoxy and R₇ is methyl.
22. A method of preparing compounds of the formulae:

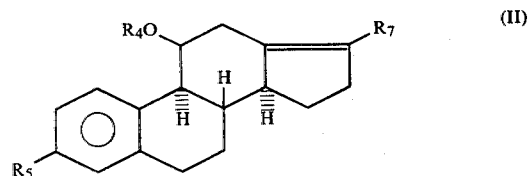

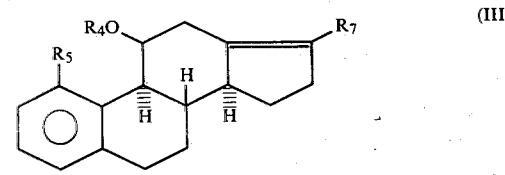

from the compound:

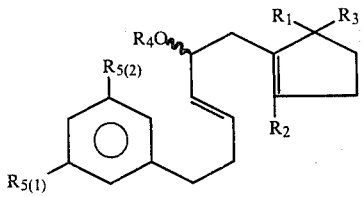

(I)

wherein:
(a) $R_1$ is H or alkyl or one to four carbon atoms;
(b) $R_2$ is H or alkyl of one to four carbon atoms, with the proviso that $R_1$ is H when $R_2$ is alkyl, and with the proviso that $R_2$ is H when $R_2$ is alkyl;
(c) $R_3$ is a suitable leaving group selected from the group consisting of hydroxy, alkoxy of one to four carbons, alkoxyalkoxy of two to four carbons, acyloxy of one to about seven carbons, and trialkylsilyloxy of less than fifteen carbons;
(d) $R_4$ is H;
(e) $R_{5(1)}$ and $R_{5(2)}$ are each H, OH, alkyl of one to eight carbons or optionally esterified or etherified hydroxy selected from the group consisting of hydroxy, alkoxy of two to four atoms, alkoxyalkoxy of two to four carbons, trialkylsilyloxy of one to fifteen carbons, cycloalkoxy of four to eight carbons, carboxyacyloxy of one to seven carbons or heterocyclic ether of five to seven atoms and four to six carbons, with the proviso that at least one of $R_{5(1)}$ and $R_{5(2)}$ is hydrogen; and
(f) $R_7$ is alkyl of one to about four carbon atoms;
which comprises the step of:
cyclising compound I in a suitable solvent with an effective amount of one or more of the acids consisting of the suitable protic and suitable aprotic Lewis acids at a temperature below about room temperature and above about −150° C.

23. The method of claim 22 wherein the cyclisaton takes place from about +10° C. to about −100° C.

24. The method of claim 22 wherein an aprotic Lewis acid is used.

25. The method of claim 24 wherein the amount of Lewis acid employed is from about 0.5 to about 5 moles per mole of compound (I).

26. The method of claim 22 wherein a protic Lewis acid is used.

27. The method of claim 26 wherein the protic Lewis acid employed has a pK(20° C.) of less than about 2.

28. A compound of the formula:

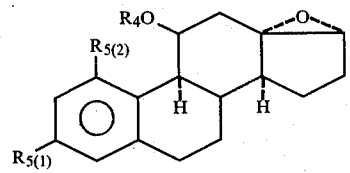

wherein $R_4$ is H, and
$R_{5(1)}$ and $R_{5(2)}$ are each H, alkyl of one to eight carbons, or an optionally esterified or etherified hydroxy group selected from the group consisting of hydroxy, alkoxy of one to four carbons, alkoxyalkoxy of two to four carbons, trialkylsilyloxy of one to fifteen carbons, cycloalkoxy of four to eight carbons, carboacyloxy of one to seven carbons, or heterocyclic ether of five to seven atoms and four to six carbon atoms, with the proviso that at least one of $R_{5(1)}$ and $R_{5(2)}$ is H.

* * * * *